United States Patent
Nakai et al.

(10) Patent No.: US 9,233,904 B2
(45) Date of Patent: Jan. 12, 2016

(54) METHOD FOR PRODUCING POLYOXYALKYLENE ALKYL ETHER CARBOXYLIC ACID OR SALT THEREOF

(71) Applicant: Kao Corporation, Tokyo (JP)

(72) Inventors: Takeshi Nakai, Wakayama (JP); Toku Fujioka, Wakayama (JP); Yasuo Amishige, Prachinburi (TH)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/369,628

(22) PCT Filed: Nov. 27, 2012

(86) PCT No.: PCT/JP2012/007599
§ 371 (c)(1),
(2) Date: Jun. 27, 2014

(87) PCT Pub. No.: WO2013/099109
PCT Pub. Date: Jul. 4, 2013

(65) Prior Publication Data
US 2015/0025271 A1 Jan. 22, 2015

(30) Foreign Application Priority Data
Dec. 28, 2011 (JP) ................. 2011-289567

(51) Int. Cl.
| | | |
|---|---|---|
| *C07C 51/23* | (2006.01) | |
| *C07C 59/125* | (2006.01) | |
| *C08G 65/324* | (2006.01) | |
| *C11D 1/06* | (2006.01) | |
| *C07C 51/25* | (2006.01) | |
| *B01J 23/644* | (2006.01) | |

(52) U.S. Cl.
CPC ............. *C07C 51/25* (2013.01); *B01J 23/6447* (2013.01); *C07C 51/23* (2013.01); *C08G 65/324* (2013.01); *C11D 1/06* (2013.01)

(58) Field of Classification Search
None
See application file for complete search history.

(56) References Cited

U.S. PATENT DOCUMENTS

| | | |
|---|---|---|
| 5,292,940 A | 3/1994 | Noack et al. |
| 2012/0296115 A1 | 11/2012 | Shirasawa et al. |

FOREIGN PATENT DOCUMENTS

| | | |
|---|---|---|
| AU | 21469/88 A | 3/1989 |
| JP | 62-198641 A | 9/1987 |
| JP | 1-146840 A | 6/1989 |
| JP | 5-503686 A | 6/1993 |
| JP | 7-5511 B2 | 1/1995 |
| JP | 2011-136933 A | 7/2011 |
| JP | 2011-184379 A | 9/2011 |
| JP | 2011-184380 A | 9/2011 |
| WO | WO 2011/081063 A1 | 7/2011 |

OTHER PUBLICATIONS

International Search Report for PCT/JP2012/007599 mailed on Mar. 5, 2013.
International Preliminary Report on Patentability and the English translation of the Written Opinion of the International Searching Authority, dated Jul. 10, 2014, for International Application No. PCT/2012/007599.

*Primary Examiner* — Yevegeny Valenrod
(74) *Attorney, Agent, or Firm* — Birch, Stewart, Kolasch & Birch, LLP

(57) ABSTRACT

A method for producing polyoxyalkylene alkyl ether carboxylic acid or a salt thereof includes an oxidation reaction process of oxidizing polyoxyalkylene alkyl ether with oxygen by supplying an oxygen-containing gas to a suspension or a solution that has a depth of 200 mm or more and includes polyoxyalkylene alkyl ether. In the oxidation reaction process, a supply rate of the oxygen-containing gas is reduced in a period in which the conversion is greater than or equal to 50% and less than 70%.

17 Claims, 1 Drawing Sheet

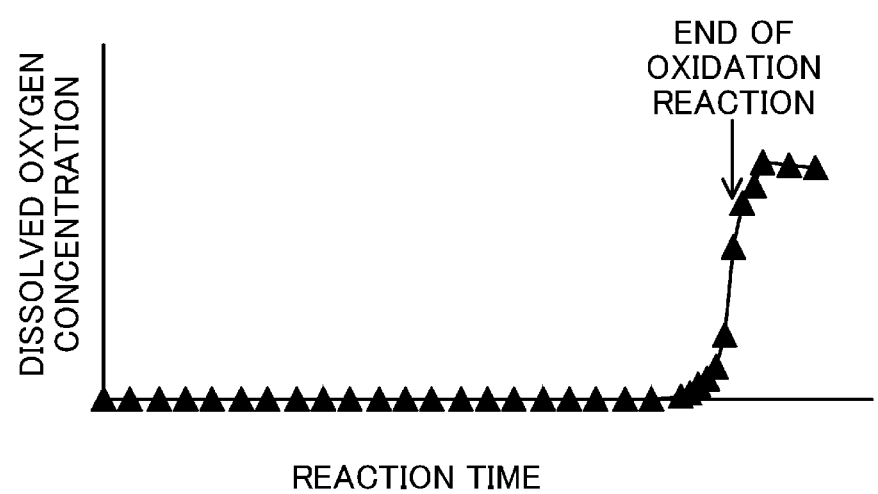

METHOD FOR PRODUCING POLYOXYALKYLENE ALKYL ETHER CARBOXYLIC ACID OR SALT THEREOF

TECHNICAL FIELD

The present invention relates to a method for producing polyoxyalkylene alkyl ether carboxylic acid or a salt thereof.

BACKGROUND ART

Polyoxyalkylene alkyl ether carboxylic acid and salts thereof are compounds produced by substituting polyoxyalkylene alkyl ether with a carboxyl group at the terminal end of the ether, exhibit high degrees of foaming and emulsification, and are known as surfactants used in cosmetics, emulsifiers, solubilizers, dispersants, gelling agents, and detergent bases, for example. Properties of polyoxyalkylene alkyl ether carboxylic acid and salts thereof can be modified by changing pH. Polyoxyalkylene alkyl ether carboxylic acid and salts thereof have excellent stability against hard water, and aqueous solutions thereof are stable to various polyvalent metal ions such as aluminium ions, are gentle to the skin, and have small inhibitory effects on enzymes. Polyoxyalkylene alkyl ether carboxylic acid and salts thereof are thus expected to have various applications.

There have been various known methods for producing polyoxyalkylene alkyl ether carboxylic acid or a salt thereof. One of such methods is a method in which polyoxyalkylene alkyl ether is oxidized with oxygen in the presence of a catalyst in which a noble metal is supported (see, for example, Patent Document 1).

Patent Documents 2 and 3 describe methods for producing salts of polyoxyalkylene alkyl ether carboxylic acid by supplying oxygen to a suspension containing polyoxyalkylene alkyl ether, a noble metal catalyst, and an alkaline material to cause catalytic oxidation of polyoxyalkylene alkyl ether. In these methods, an oxygen supply starts after the amount of dissolved oxygen in the suspension has been set at 0-1 ppm, and then the amount of dissolved oxygen in the suspension is kept in the range more than 0 ppm and less than or equal to 1 ppm.

Patent Document 4 shows a method for producing a salt of polyoxyalkylene alkyl ether carboxylic acid by using a continuous stirred tank reactor.

CITATION LIST

Patent Documents

[Patent Document 1] Japanese Unexamined Patent Publication No. S62-198641
[Patent Document 2] Japanese Unexamined Patent Publication No. 2011-184379
[Patent Document 3] Japanese Unexamined Patent Publication No. 2011-184380
[Patent Document 4] Japanese Unexamined Patent Publication No. 2011-136933

SUMMARY OF THE INVENTION

The present invention relates to a method for producing polyoxyalkylene alkyl ether carboxylic acid or a salt thereof, and the method includes an oxidation reaction process of oxidizing polyoxyalkylene alkyl ether with oxygen by supplying an oxygen-containing gas to a suspension or a solution that has a depth of 200 mm or more and includes polyoxyalkylene alkyl ether, wherein in the oxidation reaction process, in a period in which a conversion expressed by Equation (A) is greater than or equal to 50% and less than 70%, a supply rate of the oxygen-containing gas is reduced such that a supply rate of oxygen to a total mole number of polyoxyalkylene alkyl ether, polyoxyalkylene alkyl ether carboxylic acid, and the salt thereof is reduced from a range greater than 10 mol %/h and less than or equal to 15 mol %/h to a range greater than or equal to 1 mol %/h and less than or equal to 10 mol %/h, $$\text{conversion (\%)} = c_2 \times 100/(c_1 + c_2) \quad (A)$$

[where $c_1$ is a molarity (mol/L) of polyoxyalkylene alkyl ether, and
$c_2$ is a total molarity (mol/L) of polyoxyalkylene alkyl ether carboxylic acid and the salt thereof].

BRIEF DESCRIPTION OF THE DRAWINGS

FIG. 1 is a graph showing a relationship between a reaction time and a dissolved oxygen concentration.

DESCRIPTION OF EMBODIMENTS

An embodiment will be hereinafter described in detail. This embodiment is intended to include both the case of producing polyoxyalkylene alkyl ether carboxylic acid under acid conditions and the case of producing a salt of polyoxyalkylene alkyl ether carboxylic acid under alkaline conditions.

A method for producing polyoxyalkylene alkyl ether carboxylic acid or a salt thereof according to this embodiment includes an oxidation reaction process of oxidizing polyoxyalkylene alkyl ether with oxygen by supplying a gas containing oxygen (hereinafter referred to as an "oxygen-containing gas") to a suspension or a solution that has a depth of 200 mm or more and includes polyoxyalkylene alkyl ether and a catalyst. In the oxidation reaction process, in a period in which a conversion expressed by Equation (A) (hereinafter simply referred to as a "conversion") is greater than or equal to 50% and less than 70%, a supply rate of the oxygen-containing gas is reduced, $$\text{conversion (\%)} = c_2 \times 100/(c_1 + c_2) \quad (A)$$

[where $c_1$ is a molarity (mol/L) of polyoxyalkylene alkyl ether, and
$c_2$ is a total molarity (mol/L) of polyoxyalkylene alkyl ether carboxylic acid and the salt thereof].

In general, to perform catalytic oxidation of polyoxyalkylene alkyl ether in the presence of a noble metal catalyst, an oxygen-containing gas is supplied as an oxidizer to a suspension or a solution including polyoxyalkylene alkyl ether. Oxygen supplied to the suspension or the solution is consumed in the suspension or the solution during oxidation reaction.

However, when the reaction rate decreases with progress of oxidation reaction, the amount of oxygen supply exceeds the amount of oxygen consumed in the suspension or the solution, and unconsumed oxygen causes considerable bubbling of the suspension or the solution. In addition, since the product generated by the reaction is a surfactant, the bubbling becomes more considerable in a late stage of reaction in which the amount of the product is large. This considerable bubbling of the suspension or the solution disadvantageously makes it difficult to continue production because of an overflow of foaming liquid from a reaction vessel in large and deep reaction equipment.

On the other hand, when the amount of oxygen supply is controlled from a start of reaction and the amount of oxygen supply decreases below the amount of oxygen consumed in the suspension or the solution, the reaction rate decreases, and if the reaction rate considerably decreases, the reaction time extends. The extension of the reaction time deteriorates the quality, such as a hue, of the reaction product (see, for example, Patent Document 4).

In view of this problem, it is desired to suppress bubbling of the suspension or the solution in producing polyoxyalkylene alkyl ether carboxylic acid or the salt thereof.

In the method for producing polyoxyalkylene alkyl ether carboxylic acid or the salt thereof according to this embodiment, the supply rate of the oxygen-containing gas is reduced in the period in which the conversion is greater than or equal to 50% and less than 70%. Thus, in producing polyoxyalkylene alkyl ether carboxylic acid or the salt thereof in the suspension or the solution whose depth is 200 mm or more, bubbling of the suspension or the solution can be suppressed. Consequently, production can continue without an interruption by bubbling of the suspension or the solution, resulting in efficient and stable production of polyoxyalkylene alkyl ether carboxylic acid or the salt thereof.

[Oxidation Reaction Process]

In the method for producing polyoxyalkylene alkyl ether carboxylic acid or the salt thereof of this embodiment, the oxygen-containing gas is supplied to the suspension or the solution including polyoxyalkylene alkyl ether to oxidize polyoxyalkylene alkyl ether with oxygen, thereby producing polyoxyalkylene alkyl ether carboxylic acid or the salt thereof.

In method for producing polyoxyalkylene alkyl ether carboxylic acid or the salt thereof of this embodiment, the depth of the suspension or the solution is 200 mm or more, preferably 210 mm or more, and more preferably 220 mm or more, from the viewpoint of production efficiency. The depth of the suspension of the solution is preferably 10000 mm or less, more preferably 5000 mm or less, and much more preferably 1000 mm or less, from the viewpoint of production stability. From the viewpoints of production efficiency and production stability, the depth of the suspension or the solution is preferably 200-10000 mm, more preferably 210-5000 mm, and much more preferably 220-1000 mm. The depth of the suspension or the solution in this embodiment is a depth from the interface between a suspension phase or a liquid phase and a gas phase in a static state at an end of supply of a reaction material to the deepest position of the inner wall of a reaction vessel.

In the method for producing polyoxyalkylene alkyl ether carboxylic acid or the salt thereof of this embodiment, bubbling of the suspension or the solution is more suppressed as the depth of the suspension or the solution increases as long as the depth of the suspension or the solution is 200 mm or more. As the depth of the suspension or the solution increases, the amount of the suspension or the solution per the interface between the suspension phase or the liquid phase and the gas phase increases. Thus, an excessive amount of the oxygen-containing gas is not likely to flow out of the suspension phase or the liquid phase, and is likely to remain. Accordingly, bubbling of the suspension or the solution is expected to increase as the depth of the suspension or the solution increases.

(Suspension or Solution)

<Reaction Material and Reaction Product>

The suspension or the solution contains polyoxyalkylene alkyl ether as the reaction material.

After a start of reaction, the suspension or the solution contains polyoxyalkylene alkyl ether carboxylic acid and/or the salt thereof, each of which is the reaction product.

Polyoxyalkylene alkyl ether is preferably a compound expressed by formula (I):

$$RO\text{-}(AO)_n\text{-}H \qquad (I)$$

[where R is a hydrocarbon group having 4-30 carbon atoms, AO is an alkyleneoxy group having 2-4 carbon atoms, and n is an average addition mole number of AO and is 1-100.]

The structure in the formula may be appropriately selected depending on, for example, performance and application of target carboxylic acid or the salt thereof.

The number of carbon atoms in R is 4 or more, and from the viewpoints of enhancing suppression of bubbling and obtaining a high degree of emulsification of carboxylic acid or the salt thereof, is preferably 8 or more, more preferably 10 or more, and much more preferably 12 or more. On the other hand, the number of carbon atoms in R is 30 or less, and from the viewpoints of obtaining a high degree of emulsification of carboxylate or the salt thereof, is preferably 22 or less, more preferably 18 or less, and much more preferably 14 or less.

The number of carbon atoms in R is 4-30, and from the viewpoints of enhancing suppression of bubbling and obtaining high degrees of foaming and emulsification of carboxylic acid or the salt thereof, is preferably 8-22, more preferably 10-18, and much more preferably 12-14. Examples of the hydrocarbon group as R include an alkyl group and an alkenyl group. R may be linear or branched, and may be a primary or secondary group.

From the viewpoints of enhancing suppression of bubbling and obtaining high degrees of foaming and emulsification of carboxylic acid or the salt thereof, R is preferably a linear or branched primary or secondary alkyl or alkenyl group, more preferably a linear primary or secondary alkyl or alkenyl group, much more preferably a linear primary alkyl or alkenyl group, and still more preferably a linear primary alkyl group.

AO is an alkyleneoxy group having 2-4 carbon atoms, and from the viewpoints of versatility as a raw material and economic efficiency, is preferably an ethyleneoxy group having 2 carbon atoms, and more preferably 80% or more, by mole, of the total of AOs are ethyleneoxy groups.

In the formula, n is 1-100, and from the viewpoints of enhancing suppression of bubbling and obtaining high degrees of foaming and emulsification of carboxylic acid or the salt thereof, is preferably 1-20, and more preferably 2-10.

The suspension or the solution may contain only a single type of polyoxyalkylene alkyl ether, or may include a plurality of types of polyoxyalkylene alkyl ether.

From the viewpoint of obtaining a high production efficiency, the concentration of polyoxyalkylene alkyl ether in the suspension or the solution is preferably 1% by mass or more, more preferably 5% by mass or more, and much more preferably 10% or more. On the other hand, from the viewpoint of ease of handling, the concentration of polyoxyalkylene alkyl ether is preferably 40% by mass or less, more preferably 35% by mass or less, and much more preferably 30% by mass or less.

From the foregoing viewpoints, the concentration of polyoxyalkylene alkyl ether in the suspension or the solution is preferably 1-40% by mass, more preferably 5-35% by mass, and much more preferably 10-30% by mass.

The structure of polyoxyalkylene alkyl ether carboxylic acid or the salt thereof as the reaction product in production using the compound expressed by formula (I) as polyoxyalkylene alkyl ether can be expressed by formula (II):

$$\{RO\text{-}(AO)_{n-1}\text{-}A'\text{-}COO\}_m M \qquad (II)$$

[where R, AO, and n are the same as in formula (I), A' is an alkylene group having 1-3 carbon atoms, M is a cation or a hydrogen ion, and m is a valence of M.]

Preferable forms of R, AO, and n in formula (II) are the same as those in formula (I).

In the above formula, A' is an alkylene group having 1-3 carbon atoms. The structure of -A'-COO— is formed by oxidation of the terminal-AO— of formula (I). Thus, A' has a smaller carbon atom numbers by one than the terminal-AO— in formula (I).

Examples of M as cation include alkali metal ions, alkali earth metal ions, ammonium ions, and hydrogen ions. Examples of alkali metal ions include lithium ions, sodium ions, and potassium ions. Examples of alkali earth metal ions include magnesium ions and calcium ions. From the viewpoints of appropriate viscosity of the suspension or the solution during production and convenience of production processes, M serving as cation is more preferably alkali metal ions or hydrogen ions. From the viewpoint of reduction of production cost, alkali metal ions are preferably sodium ions or potassium ions, and more preferably potassium ions.

<Noble Metal-supported Catalyst>

The suspension or the solution may be a suspension including a powdery noble metal-supported catalyst in which a noble metal is supported on a support.

From the viewpoint of obtaining a high yield of polyoxyalkylene alkyl ether carboxylic acid or the salt thereof, the noble metal as the catalyst preferably includes at least one element selected from elements of a platinum group, specifically preferably includes at least one element selected from the group consisting of ruthenium, rhodium, palladium, osmium, iridium, and platinum, and more preferably includes at least one element selected from the group consisting of palladium and platinum.

In the case where the noble metal includes at least one element selected from the platinum group (hereinafter referred to as a "first catalyst component"), the noble metal-supported catalyst preferably further includes, as a catalyst component, at least one element selected from the group consisting of tin, bismuth, selenium, tellurium, and antimony (hereinafter referred to as a "second catalyst component").

In the case where the noble metal-supported catalyst includes the first catalyst component and the second catalyst component, the noble metal-supported catalyst preferably further includes, as a catalyst component, at least one element selected from the group consisting of rare-earth elements (hereinafter referred to as a "third catalyst component").

Examples of the support supporting the catalyst component including the noble metal of the first catalyst component include inorganic supports such as activated charcoal, alumina, silica gel, activated clay, and diatomaceous earth. Among these inorganic supports, activated charcoal is preferred from the viewpoint of high resistance against an acid material or an alkaline material. Activated charcoal used herein may be produced by a known method using sawdust, wood chips, charcoal, coconut husk charcoal, coal, or peat coal, for example, as a raw material.

From the viewpoint of obtaining a high yield of polyoxyalkylenE0020alkyl ether carboxylic acid or the salt thereof, the amount of the supported noble metal of the first catalyst component in the noble metal-supported catalyst is preferably 0.1% by mass or more, more preferably 0.5% by mass or more, and much more preferably 1% by mass or more, of the entire noble metal-supported catalyst, and on the other hand, is preferably 20% by mass or less, more preferably 15% by mass or less, and much more preferably 10% by mass or less, of the entire noble metal-supported catalyst.

From the foregoing viewpoints, the amount of the supported noble metal is preferably 0.1-20% by mass, more preferably 0.5-15% by mass, and much more preferably 1-10% by mass.

The noble metal-supported catalyst can be produced by a known method described in, for example, Japanese Unexamined Patent Publication No. S62-269746. For example, each catalyst component is adsorbed on the support in an aqueous solution of a compound containing the first catalyst component (e.g., palladium chloride or platinum chloride), an aqueous solution of a compound containing the second catalyst component (e.g., bismuth chloride or antimony pentachloride) when necessary, and an aqueous solution of a compound containing the third catalyst component (e.g., cerium chloride or lanthanum chloride) when necessary, and then the catalyst components are reduced to obtain the noble metal-supported catalyst.

The form of the catalyst produced by the above-described method is not specifically limited, and the form of the catalyst except the powdery form described above may be those described in, for example, Table 19.5 of "Kagaku Kougaku Binran, 6th edition" (Maruzen), p. 993.

The content of the noble metal of the first catalyst component in the suspension is preferably 0.001-2.0% by mass, more preferably 0.01-1.5% by mass, and much more preferably 0.02-1.3% by mass, of the content of polyoxyalkylene alkyl ether, which is the reaction material. In the case where a plurality of elements are included as first catalyst components, the content of the noble metal is the total amount of these elements.

From the viewpoint of enhancing reactivity to polyoxyalkylene alkyl ether, the content of the noble metal-supported catalyst in the suspension is preferably 0.1% by mass or more, more preferably 0.5% by mass or more, and much more preferably 1% by mass or more. On the other hand, from the economic viewpoint, the content of the noble metal-supported catalyst is preferably 20% by mass or less, more preferably 15% by mass or less, and much more preferably 10% by mass or less. From the foregoing viewpoints, the content of the noble metal-supported catalyst in the suspension is preferably 0.1-20% by mass, more preferably 0.5-15% by mass, and much more preferably 1-10% by mass.

<Water>

The suspension or the solution includes water.

From the viewpoints of high reactivity and ease of handling, the content of water in the suspension or the solution is preferably 0.1-100 as large as, by mass, more preferably 0.5-50 as large as, by mass, and much more preferably 1-20 as large as, by mass of, the content of polyoxyalkylene alkyl ether.

The suspension or the solution may include an organic solvent of, for example, lower alcohol such as ethanol as long as the reactivity does not decrease and the solvent does not inhibit foaming after being mixed in, for example, a detergent.

<Alkaline Material>

In the case of producing polyoxyalkylene alkyl ether carboxylate under alkaline conditions, the suspension or the solution preferably includes an alkaline material. Oxidation of polyoxyalkylene alkyl ether with oxygen is preferably performed in the presence of the alkaline material.

Examples of the alkaline material include: alkali metal hydroxides such as sodium hydroxide and potassium hydroxide; and alkali metal carbonates such as sodium carbonate and potassium carbonate. Among these elements, from the viewpoint of obtaining high reactivity, alkali metal hydroxides are preferred. Among alkali metal hydroxides, sodium hydroxide and potassium hydroxide are preferred, and sodium hydroxide is more preferred.

The suspension or the solution may include only one type of the alkaline material, or may include a plurality of types of alkaline materials.

The content of the alkaline material in the suspension or the solution is preferably such that the pH of the suspension or the solution is 7-14, more preferably such that the pH of the suspension or the solution is 9-14, and much more preferably such that the pH of the suspension or the solution is 11-14.

<Optional Component>

The suspension or the solution may previously include polyoxyalkylene alkyl ether carboxylic acid, which is the product of oxidation reaction of polyoxyalkylene alkyl ether, and/or the salt thereof. The suspension or the solution may additionally include an organic solvent, an inorganic salt, and/or polymer, for example, as long as reactivity does not decrease, foaming power does not decrease when being mixed in, for example, a detergent, and separation removal of the noble metal-supported catalyst included in a reaction liquid is not inhibited.

The suspension or the solution may include an antifoaming agent. Examples of the antifoaming agent include silicone oil, higher alcohol, higher fatty acid and the salt thereof, pluronic copolymer, tetronic copolymer, polyethylene glycol, and polypropylene glycol. In the case where polyoxyalkylene alkyl ether carboxylic acid produced or the salt thereof is to be used for a detergent, from the viewpoint of preventing weakening of foaming of the detergent composition, the suspension and the solution preferably includes no antifoaming agent.

<Properties of Suspension or Solution>

Before oxidation reaction of the suspension or the solution, i.e., at a start of the oxygen-containing gas supply, the dissolved oxygen concentration is preferably less than 3.0 mg/L and more preferably 1.0 mg/L or less. The dissolved oxygen concentration of the suspension or the solution is measured with various types of measurement devices based on a measurement principle of a corneal electrode type (e.g., a polarography type or a galvanic cell type) or a fluorescence type by immersing a measurement sensor in the suspension or the solution.

The suspension or the solution is non-Newtonian pseudoplastic fluid whose viscosity varies depending on the conversion or the temperature and whose apparent viscosity decreases as an applied shear rate increases. Thus, the apparent viscosity of the suspension or the solution before start of reaction (i.e., before an oxygen supply) affects reactivity, i.e., reaction end time. Accordingly, from the viewpoint of productivity, and in addition, from the viewpoint of quality such as hue, the apparent viscosity before start of reaction of the suspension or the solution (i.e., before the oxygen supply) is preferably 1-10000 mPa·s, more preferably 10-5000 mPa·s, much more preferably 20-1000 mPa·s, and still more preferably 30-200 mPa·s. The viscosity of the suspension or the solution is measured with a rheometer (e.g., ARES-100TNI produced by TA instruments Inc.) as a static viscosity with Couette 34 mm being attached under conditions of 70° C. and a shear rate of $1\ s^{-1}$.

From the viewpoint of reactivity and quality such as hue, the pH of the suspension or the solution is preferably 7-14, more preferably 9-14, and much more preferably 11-14 in the case of producing polyoxyalkylene alkyl ether carboxylic acid or the salt thereof.

(Oxidation Reaction)

<Oxygen-containing Gas>

From the viewpoint of increasing the reaction rate and the viewpoint of reducing bubbling of the suspension or the solution by reducing a component included in the oxygen-containing gas and not consumed by reaction, the oxygen concentration of the oxygen-containing gas is preferably 50% by volume or more, more preferably 80% by volume or more, much more preferably 85% by volume or more, and still more preferably 90% by volume or more. Examples of a technique for obtaining the oxygen-containing gas with a high oxygen concentration include cryogenic air separation using air as a raw material, pressure swing adsorption, and membrane separation. Among these techniques, from the viewpoints of easiness in production and economic efficiency, pressure swing adsorption is often employed. The upper limit of the oxygen concentration in the oxygen-containing gas is 100% by volume. In the case of pressure swing adsorption, the principle of this technique makes it difficult to remove argon in the air, and thus, the oxygen concentration is about 96% by volume at maximum.

Thus, from the viewpoint of productivity of polyoxyalkylene alkyl ether carboxylic acid or the salt thereof, the oxygen concentration is preferably 96% by volume or less and more preferably 92% by volume or less.

From the foregoing viewpoints, the oxygen concentration is preferably 50-100% by volume, more preferably 80-96% by volume, much more preferably 85-96% by volume, still more preferably 90-96% by volume, and yet more preferably 90-92% by mass.

Examples of a gas except oxygen in the oxygen-containing gas include nitrogen and rare gases such as argon that are inert in oxidation reaction of polyoxyalkylene alkyl ether.

<Supply of Oxygen-containing Gas to Suspension or Solution>

The Oxygen-Containing Gas to the Suspension or the Solution is Supplied by Blowing the oxygen-containing gas into the suspension or the solution in, for example, a stirred tank reactor. This blowing of the oxygen-containing gas to the suspension or the solution may be continuous or intermittent, but from the viewpoint of production efficiency, the blowing is preferably continuous.

From the viewpoint of enhancing the reaction rate by diffusing oxygen in the suspension or the solution, a ratio (d/D) of a depth (d) at which the oxygen-containing gas is supplied to the suspension or the solution, from the liquid level in a static state at the end of filling with the reaction material, to the depth (D) of the suspension or the solution is preferably 0.1-1, more preferably 0.5-1, much more preferably 0.9-1, and still more preferably 1.

It is known that bubbling of a suspension or a solution is caused by unconsumed oxygen when the amount of oxygen supply exceeds the amount of oxygen consumed in the suspension or the solution. In view of this, bubbling of the suspension or the solution was considered to become less serious as an initial supply rate of an oxygen-containing gas decreases. However, surprisingly, the supply rate is found to be preferably in the following range. From the viewpoints of productivity and avoiding bubbling of the suspension or the solution, the initial supply rate of the oxygen-containing gas to the suspension or the solution in the method for producing polyoxyalkylene alkyl ether carboxylic acid or the salt thereof of this embodiment is set such that the oxygen supply rate to the total mole number of polyoxyalkylene alkyl ether, polyoxyalkylene alkyl ether carboxylic acid, and the salt thereof is higher than 10 mol %/h and is preferably 11 mol %/h or higher.

Although the reasons are unclear, this is considered to be because of the following reasons.

An aqueous solution with some composition of polyoxyalkylene alkyl ether, polyoxyalkylene alkyl ether carboxylic acid, and/or the salt thereof forms liquid crystal having a high static viscosity. When a liquid phase component in the suspension or the solution comes to have such a composition during reaction, an apparent viscosity of the suspension or the solution increases. Part of the oxygen-containing gas supplied to the suspension or the solution that was not consumed in the reaction is likely to remain in the suspension or the solution having an increased apparent viscosity. In addition, part of the gas mixed in the liquid phase by stirring is not likely to be released from the suspension or the solution, and the suspension or the solution bubbles.

Accordingly, for a composition of the liquid phase component with the high static viscosity, from the viewpoint of reducing the amount of air remaining in the suspension or the solution so as to avoid bubbling, the initial supply rate of the oxygen-containing gas is preferably set in the above-described range in order to facilitate reaction.

On the other hand, to maintain the reaction rate, the initial supply rate of the oxygen-containing gas is set such that the supply rate of oxygen to the total mole number of polyoxyalkylene alkyl ether, polyoxyalkylene alkyl ether carboxylic acid, and the salt thereof is 15 mol %/h or less.

From the foregoing viewpoints, the supply rate of the oxygen-containing gas to the suspension or the solution is set such that the supply rate of oxygen to the total mole number of polyoxyalkylene alkyl ether, polyoxyalkylene alkyl ether carboxylic acid, and the salt thereof is higher than 10 mol %/h and less than or equal to 15 mol %/h, and more preferably higher than 11 mol %/h and less than or equal to 15 mol %/h. The supply rate of the oxygen-containing gas preferably continuously falls within the above-described range, but may be temporarily out of the range as long as advantages obtained by the method for producing polyoxyalkylene alkyl ether carboxylic acid or the salt thereof of this embodiment are not impaired.

The supply rate of the oxygen-containing gas to the suspension or the solution is reduced while the conversion is higher than 50% and less than 70%. From the viewpoint of reducing bubbling of the suspension or the solution, the supply rate of the oxygen-containing gas to the suspension or the solution is reduced when the conversion is 50% or more, more preferably 53% or more, and much more preferably 55% or more. On the other hand, from the viewpoint of productivity, the supply rate of the oxygen-containing gas is reduced when the conversion is less than 70%, more preferably 67% or less, and much more preferably 65% or less.

Reduction of the supply rate of the oxygen-containing gas to the suspension or the solution may be performed only once, or may be performed in a plurality of steps at a plurality of stages from the viewpoint of maintaining the reaction rate.

The oxygen-containing gas is blown into the suspension or the solution through an outlet of a gas blowing pipe placed in the suspension or the solution. Examples of the outlet of the gas blowing pipe include a single-hole nozzle, a multi-pole nozzle, and a ring-shaped nozzle.

From the viewpoint of productivity, the supply rate of the oxygen-containing gas after reduction of the supply rate of the oxygen-containing gas to the suspension or the solution is set such that the supply rate of oxygen to the total mole number of polyoxyalkylene alkyl ether, polyoxyalkylene alkyl ether carboxylic acid, and the salt thereof is 1 mol %/h or more, more preferably 2 mol %/h or more, and much more preferably 5 mol %/h or more. On the other hand, from the viewpoint of maintaining the reaction rate, the supply rate after reduction of the supply rate of the oxygen-containing gas is set such that the supply rate of oxygen to the total mole number of polyoxyalkylene alkyl ether, polyoxyalkylene alkyl ether carboxylic acid, and the salt thereof is 10 mol %/h or less and preferably 8 mol %/h or less.

From the foregoing viewpoints, the supply rate of the oxygen-containing gas after reduction of the supply rate of the oxygen-containing gas to the suspension or the solution is set such that the supply rate of oxygen to the total mole number of polyoxyalkylene alkyl ether, polyoxyalkylene alkyl ether carboxylic acid, and the salt thereof is 1-10 mol %/h, preferably 2-8 mol %/h, and more preferably 5-8 mol %/h.

In blowing the oxygen-containing gas into the suspension or the solution, the suspension or the solution is preferably stirred with a stirring impeller in the stirred tank reactor. A PV value, which is an index of the stirring efficiency, is preferably 0.1 or more, more preferably 0.2 or more, and much more preferably 0.5 or more. The PV value herein refers to power necessary for stirring per a unit volume of the suspension or the solution, and is defined as a rate of the stirring power (kW) obtained by subtracting a friction loss due to stirring from power of an agitator, i.e., actually transmitted to the suspension or the solution, to a volume ($m^3$) of the suspension or the solution.

Examples of the stirring impeller for stirring include a paddle impeller, a turbine impeller, and a propeller impeller. Examples of the paddle impeller include an impeller including a flat plate-like member and an anchor impeller. In the paddle impeller including a flat plate-like member, the ratio (S2/S1) of a maximum projected area (S2) viewed in a direction perpendicular to a rotation axis of a shaft of the stirring impeller to a maximum cross section (S1) of a vertical plane of an area occupied by a liquid phase portion in the stirred tank reactor is preferably 0.10-0.90 and more preferably 0.20-0.70, from the viewpoint of efficient production of polyoxyalkylene alkyl ether carboxylate or the salt thereof. Examples of a commercially available stirring impeller with such a configuration include Maxblend impeller produced by Sumitomo Heavy Industries, Ltd., FULLZONE (trade name) produced by Kobelco Eco-Solutions Co., Ltd., and Super-Mix MR203 (trade name) produced by Satake Chemical Equipment Mfg Ltd.

From the viewpoint of maintaining the reaction rate, the supply rate of the oxygen-containing gas to the suspension or the solution and the PV value are set such that an increase rate of the conversion per an hour is preferably 50% or less, more preferably 40% or less, and much more preferably 30% or less.

From the viewpoint of enhancing reactivity to polyoxyalkylene alkyl ether, the dissolved oxygen concentration in the suspension or the solution during oxidation of polyoxyalkylene alkyl ether with oxygen is maintained at preferably 0 mg/L or more, more preferably 0.1 mg/L or more, much more preferably 0.2 mg/L or more, and still more preferably 0.3 mg/L or more. From the viewpoint of suppressing bubbling of the suspension or the solution, the dissolved oxygen concentration is maintained at preferably 1.0 mg/L or less, more preferably 0.9 mg/L or less, much more preferably 0.8 mg/L or less, and still more preferably 0.7 mg/L or less. The dissolved oxygen concentration in the suspension or the solution can be controlled by chronologically measuring the dissolved oxygen concentration in the suspension or the solution with a measurement device and also by changing the amount of the oxygen-containing gas supplied to the suspension or the solution based on the measurement result.

From the foregoing viewpoints, the dissolved oxygen concentration in the suspension or the solution during oxidation of polyoxyalkylene alkyl ether with oxygen is preferably 0-1.0 mg/L, more preferably 0.1-0.9 mg/L, much more preferably 0.2-0.8 mg/L, and still more preferably 0.3-0.7 mg/L.

The dissolved oxygen concentration may be out of the above-described ranges in oxidation of polyoxyalkylene alkyl ether with oxygen, but from the viewpoints of enhancing reactivity to polyoxyalkylene alkyl ether and suppressing bubbling of the suspension or the solution, 50% or more of the reaction time is preferably maintained in the above-described ranges, 70% or more of the reaction time is more preferably maintained in the above-described ranges, and 90% or more of the reaction time is much more preferably maintained in the above-described ranges.

The reaction temperature in oxidation of polyoxyalkylene alkyl ether with oxygen is preferably 20° C. or higher, more preferably 30° C. or higher, and much more preferably 40° C. or higher, and on the other hand, is preferably 100° C. or lower, more preferably 90° C. or lower, and much more preferably 80° C. or lower. From the foregoing viewpoints, the reaction temperature is preferably 20-100° C., more preferably 30-90° C., and much more preferably 40-80° C.

From the viewpoint of enhancing solubility of oxygen to the suspension or the solution and considering the pressure resistance of the device, the reaction pressure as a gauge pressure is preferably from 0 (ambient pressure) to 1.0 MPa, more preferably from 0 (ambient pressure) to 0.5 MPa, and much more preferably 0 (ambient pressure) to 0.3 MPa.

For example, polyoxyalkylene alkyl ether, the noble metal-supported catalyst, and water may be continuously or intermittently supplied to the stirred tank reactor. In the case of supplying the alkaline material, the alkaline material is preferably supplied as an aqueous solution, and is preferably continuously or intermittently supplied such that the pH of the suspension or the solution is maintained at a predetermined level.

Oxidation reaction may also be performed by supplying polyoxyalkylene alkyl ether, the noble metal-supported catalyst, water, the alkaline material, and the catalyst to the stirred tank reactor in which a product of a previous batch in the same reaction remains or the stirred tank reactor already filled with a product containing polyoxyalkylene alkyl ether and/or polyoxyalkylene alkyl ether carboxylic acid of the invention. In this case, the conversion expressed by Equation (A) at a start of the oxidation reaction is preferably 30% or more, more preferably 35% or more, and much more preferably 40% or more, and is preferably less than 50% and more preferably 45% or less.

The total amount of polyoxyalkylene alkyl ether, polyoxyalkylene alkyl ether carboxylic acid, and the salt thereof is preferably 1% by mass or more, more preferably 5% by mass or more, and much more preferably 15% by mass or more, and is preferably 70% by mass or less, more preferably 40% by mass or less, and much more preferably 30% by mass or less, of the total amount of the suspension or the solution. From the foregoing viewpoints, the total amount of polyoxyalkylene alkyl ether, polyoxyalkylene alkyl ether carboxylic acid, and the salt thereof is preferably is 1-70% by mass, more preferably 5-40% by mass, and much more preferably 15-30% by mass, of the total amount of the suspension or solution.

<End of Oxidation Reaction Process>

In the method for producing polyoxyalkylene alkyl ether carboxylic acid or the salt thereof of this embodiment, from the viewpoint of excellent formability as a detergent base of polyoxyalkylene alkyl ether carboxylic acid or the salt thereof, polyoxyalkylene alkyl ether carboxylic acid or the salt thereof preferably has high purity. Thus, from the viewpoint of excellent formability as the detergent base of polyoxyalkylene alkyl ether carboxylic acid or the salt thereof, the conversion at the end of oxidation reaction is preferably 80% or more, preferably 95% or more, and much more preferably 96% or more.

The total amount of polyoxyalkylene alkyl ether, polyoxyalkylene alkyl ether carboxylic acid, and the salt thereof at the end of oxidation reaction is preferably 1-100% by mass, more preferably 5-40% by mass, and much more preferably 15-30% by mass, of the total amount of the suspension or the solution.

When oxygen is supplied to the suspension or the solution including polyoxyalkylene alkyl ether, oxygen is consumed by oxidation reaction of polyoxyalkylene alkyl ether with oxygen.

When the oxidation reaction is finished, consumption of oxygen supplied to the suspension or the solution is stopped, and accordingly, oxygen supplied to the suspension or the solution remains. Consequently, oxygen that cannot be dissolved in the suspension or the solution any more causes considerable bubbling of the suspension or the solution. It is difficult to remove generated bubbles from the reactor. In addition, when the noble metal-supported catalyst is removed by separation removal with filtration in a process step of obtaining the product after reaction, the bubbles make the filtration accuracy and the filtration speed decrease. Thus, it is necessary to, for example, allow the suspension or the solution to stand until bubbles disappear or to add an antifoaming agent to the suspension or the solution beforehand. However, the former significantly reduces the production efficiency, and the later affects foaming performance of the reaction product used as a detergent. For these reasons, production of a surfactant for a detergent use does not generally employ blowing of gas into a suspension or a solution such as an aqueous solution containing the reaction product.

In view of this, in the method for producing polyoxyalkylene alkyl ether carboxylic acid or the salt thereof of this embodiment, when oxidation reaction ends, the dissolved oxygen concentration in the suspension or the solution steeply increases, as shown in FIG. 1. Thus, it is preferable to detect the steep increase in dissolved oxygen concentration as the end of oxidation reaction so that the supply of the oxygen-containing gas to the suspension or the solution is stopped upon this detection. In this manner, bubbling of the suspension or the solution after the end of oxidation reaction can be suppressed. From the viewpoint of suppressing bubbling of the suspension or the solution, the steep increase in the dissolved oxygen concentration in the suspension or the solution is such that the increase rate of the dissolved oxygen concentration in the suspension or the solution is preferably 0.3-1000 mg/L/min, more preferably 1-500 mg/L/min, and much more preferably 5-200 mg/L/min.

The dissolved oxygen concentration in the suspension or the solution during oxidation reaction is maintained preferably in the range of 0-3.0 mg/L, more preferably in the range of 0-0.2 mg/L, and much more preferably in the range of 0-1.0 mg/L. However, despite such a control of the dissolved oxygen concentration, the dissolved oxygen concentration starts increasing steeply once oxidation reaction is finished. In this case, from the viewpoint of avoiding bubbling of the suspension or the solution, the supply of the oxygen-containing gas to the suspension or the solution is stopped preferably when the dissolved oxygen concentration in the suspension or the solution exceeds 3.0 mg/L, more preferably when the dissolved oxygen concentration in the suspension or the solution exceeds 2.0 mg/L, and much more preferably when the dissolved oxygen concentration in the suspension or the solution exceeds 1.0 mg/L.

[Process Step of Obtaining Product]

In the method for producing polyoxyalkylene alkyl ether carboxylic acid or the salt thereof of this embodiment, in the case where reaction is performed in the suspension containing the powdery noble metal-supported catalyst, the suspension after the reaction is filtered, for example, thereby performing separation removal on the noble metal-supported catalyst.

In the case of producing polyoxyalkylene alkyl ether carboxylic acid under acid conditions, carboxylic acid contained in a reaction liquid after the separation removal of the noble metal-supported catalyst can be used as the product without change.

In the case of producing polyoxyalkylene alkyl ether carboxylate under alkaline conditions, part or the whole of polyoxyethylene alkyl ether carboxylic acid in the form of a salt is dissolved in the solution after separation removal of the noble metal-supported catalyst. Thus, in this case, after a pH adjustment, the obtained solution can be used as the product of the surfactant solution. Alternatively, the obtained solution may be changed into an acid form with mineral acid such as hydrochloric acid so that carboxylic acid liberated through extraction is used as a product.

The total concentration of polyoxyalkylene alkyl ether carboxylic acid and the salt thereof in the product is preferably 1-100% by mass, more preferably 5-40% by mass, and much more preferably 15-30% by mass, in an acid form.

The method for producing polyoxyalkylene alkyl ether carboxylic acid or the salt thereof of the embodiment will be described in further detail.

<1> A method for producing polyoxyalkylene alkyl ether carboxylic acid or a salt thereof, the method comprising an oxidation reaction process of oxidizing polyoxyalkylene alkyl ether with oxygen by supplying an oxygen-containing gas to a suspension or a solution that has a depth of 200 mm or more and includes polyoxyalkylene alkyl ether, wherein in the oxidation reaction process, in a period in which a conversion expressed by Equation (A) is greater than or equal to 50%, preferably greater than or equal to 53%, and more preferably greater than or equal to 55%, and is less than 70%, preferably less than or equal to 67%, and more preferably less than or equal to 65%, a supply rate of the oxygen-containing gas is reduced such that a supply rate of oxygen to a total mole number of polyoxyalkylene alkyl ether, polyoxyalkylene alkyl ether carboxylic acid, and the salt thereof is reduced from a range greater than 10 mol %/h and less than or equal to 15 mol %/h to a range greater than or equal to 1 mol %/h and less than or equal to 10 mol %/h, $$\text{conversion (\%)} = c2 \times 100/(c1+c2) \quad (A)$$

[where $c1$ is a molarity (mol/L) of polyoxyalkylene alkyl ether, and
$c2$ is a total molarity (mol/L) of polyoxyalkylene alkyl ether carboxylic acid and the salt thereof].

<2> The method described in method <1> in which in the oxidation reaction process, the supply rate of the oxygen-containing gas after reduction of the supply rate of the oxygen-containing gas is such that the supply rate of oxygen to the total mole number of polyoxyalkylene alkyl ether, polyoxyalkylene alkyl ether carboxylic acid, and the salt thereof is preferably greater than or equal to 1 mol %/h, more preferably greater than or equal to 2 mol %/h, and much more preferably greater than or equal to 5 mol %/h.

<3> The method described in method <1> or <2> in which in the oxidation reaction process, the supply rate of the oxygen-containing gas after reduction of the supply rate of the oxygen-containing gas is such that the supply rate of oxygen to the total mole number of polyoxyalkylene alkyl ether, polyoxyalkylene alkyl ether carboxylic acid, and the salt thereof is preferably less than or equal to 10 mol %/h, and more preferably less than or equal to 8 mol %/h.

<4> The method described in method <1> in which in the oxidation reaction process, the supply rate of the oxygen-containing gas after reduction of the supply rate of the oxygen-containing gas is such that the supply rate of oxygen to the total mole number of polyoxyalkylene alkyl ether, polyoxyalkylene alkyl ether carboxylic acid, and the salt thereof is preferably 1-10 mol %/h, more preferably 2-8 mol %/h, and much more preferably 5-8 mol %/h.

<5> The method described in any one of methods <1> to <4> in which a total amount of polyoxyalkylene alkyl ether, polyoxyalkylene alkyl ether carboxylic acid, and the salt thereof is preferably 1% by mass or more, more preferably 5% by mass or more, and much more preferably 15% by mass or more, of a total amount of the suspension or the solution.

<6> The method described in any one of methods <1> to <5> in which a total amount of polyoxyalkylene alkyl ether, polyoxyalkylene alkyl ether carboxylic acid, and the salt thereof is preferably 70% by mass or less, more preferably 40% by mass or less, and much more preferably 30% by mass or less, of a total amount of the suspension or the solution.

<7> The method described in any one of methods <1> to <4> in which a total amount of polyoxyalkylene alkyl ether, polyoxyalkylene alkyl ether carboxylic acid, and the salt thereof is preferably 1-70% by mass, more preferably 5-40% by mass, and much more preferably 15-30% by mass, of a total amount of the suspension or the solution.

<8> The method described in any one of methods <1> to <7> in which in the oxidation reaction process, an oxygen concentration in the oxygen-containing gas to be supplied to the suspension or the solution is preferably 50% by volume or more, more preferably 80% by volume or more, much more preferably 85% by volume or more, and still more preferably 90% by volume or more.

<9> The method described in any one of methods <1> to <8> in which in the oxidation reaction process, an oxygen concentration in the oxygen-containing gas to be supplied to the suspension or the solution is preferably 96% by volume or less and more preferably 92% by volume or less.

<10> The method described in any one of methods <1> to <7> in which in the oxidation reaction process, an oxygen concentration in the oxygen-containing gas to be supplied to the suspension or the solution is preferably 50-100% by volume, more preferably 80-96% by volume, much more preferably 85-96% by volume, still more preferably 90-96% by volume, and yet more preferably 90-92% by volume.

<11> The method described in any one of methods <1> to <10> in which in the oxidation reaction process, the conversion at the end of reaction is preferably 80% or more, more preferably 95% or more, and much more preferably 96% or more.

<12> The method described in any one of methods <1> to <11> in which the suspension or the solution including polyoxyalkylene alkyl ether contains a powdery noble metal-supported catalyst in which a noble metal is supported on a support.

<13> The method described in method <12> in which a content of the noble metal-supported catalyst in the suspension or the solution is preferably 0.1% by mass or more, more preferably 0.5% by mass or more, and much more preferably 1% by mass or more.

<14> The method described in methods <12> or <13> in which the content of the noble metal-supported catalyst in the suspension or the solution is preferably 20% by mass or less, more preferably 15% by mass or less, and much more preferably 10% by mass or less.

<15> The method described in method <12> in which the content of the noble metal-supported catalyst in the suspension or the solution is preferably 0.1-20% by mass, more preferably 0.5-15% by mass, and much more preferably 1-10% by mass.

<16> The method described in any one of methods <12> to <15> in which the noble metal is at least one element selected from elements of a platinum group.

<17> The method described in any one of methods <1> to <16> in which in the oxidation reaction process, a reaction temperature during supply of the oxygen-containing gas to the suspension or the solution is preferably 20° C. or higher, more preferably 30° C. or higher, and much more preferably 40° C. or higher.

<18> The method described in any one of methods <1> to <17> in which in the oxidation reaction process, a reaction temperature during supply of the oxygen-containing gas to the suspension or the solution is preferably 100° C. or lower, more preferably 90° C. or lower, and much more preferably 80° C. or lower.

<19> The method described in any one of methods <1> to <16> in which in the oxidation reaction process, a reaction temperature during supply of the oxygen-containing gas to the suspension or the solution is preferably 20-100° C., more preferably 30-90° C., and much more preferably 40-80° C.

<20> The method described in any one of methods <1> to <19> in which polyoxyalkylene alkyl ether carboxylate is expressed by:

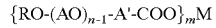

[where R is a hydrocarbon group having 4-30 carbon atoms, AO is an alkyleneoxy group having 2-4 carbon atoms, n is an average addition mole number of AO and ranges from 1 to 100, A' is an alkylene group having 1-3 carbon atoms, M is a cation or a hydrogen ion, and m is a valence of M].

<21> The method described in any one of methods <1> to <20> in which in the oxidation reaction process, the depth of the suspension or the solution is 200 mm or more, preferably 210 mm or more, and more preferably 220 mm or more.

<22> The method described in any one of methods <1> to <21> in which in the oxidation reaction process, the depth of the suspension or the solution is 10000 mm or less, preferably 5000 mm or less, and more preferably 1000 mm or less.

<23> The method described in any one of methods <1> to <20> in which in the oxidation reaction process, the depth of the suspension or the solution is 200-10000 mm, preferably 210-5000 mm, and more preferably 220-1000 mm.

<24> The method described in any one of methods <1> to <23> in which in the oxidation reaction process, a ratio (d/D) of a depth (d) at which the oxygen-containing gas is supplied to the suspension or the solution, from a liquid level in a static state at an end of filling with a reaction material, to the depth (D) to the suspension or the solution is preferably 0.1-1, more preferably 0.5-1, much more preferably 0.9-1, and still more preferably 1.

<25> The method described in any one of methods <1> to <24> in which in the oxidation reaction process, when a dissolved oxygen concentration in the suspension or the solution steeply increases, supply of the oxygen-containing gas to the suspension or the solution is stopped.

<26> The method described in any one of methods <1> to <25> in which in the oxidation reaction process, until a dissolved oxygen concentration in the suspension or the solution steeply increases, the dissolved oxygen concentration in the suspension or the solution is maintained preferably in a range of 0-3.0 mg/L, more preferably in a range of 0-0.2 mg/L, and much more preferably in a range of 0-1.0 mg/L.

<27> The method described in any one of methods <1> to <26> in which in the oxidation reaction process, when a dissolved oxygen concentration in the suspension or the solution steeply increases and exceeds preferably 3.0 mg/L, more preferably 2.0 mg/L, and much more preferably 1.0 mg/L, supply of the oxygen-containing gas to the suspension or the solution is stopped.

<28> The method described in any one of methods <1> to <27> in which in the oxidation reaction process, an increase rate of a dissolved oxygen concentration in the suspension or the solution when the dissolved oxygen concentration in the suspension or the solution steeply increases is preferably 0.3-1000 mg/L/min, more preferably 1-500 mg/L/min, and much more preferably 5-200 mg/L/min.

<29> The method described in any one of methods <1> to <28> in which in the oxidation reaction process, a supply rate of the oxygen-containing gas to the suspension or the solution is reduced in a plurality of steps at a plurality of stages.

<30> The method described in any one of methods <1> to <29> in which in the oxidation reaction process, the suspension or the solution is a suspension.

<31> The method described in any one of methods <1> to <30> in which in the oxidation reaction process, polyoxyalkylene alkyl ether, a noble metal-supported catalyst, water, alkali, and a catalyst are supplied to a stirred tank reactor in which a product in a previous batch in the same reaction remains or a stirred tank reactor in which a product containing polyoxyalkylene alkyl ether and/or polyoxyalkylene alkyl ether carboxylic acid of the invention obtained in another batch has been already charged.

<31> The method described in method <31> in which in the oxidation reaction process, the conversion expressed by Equation (A) at a start of oxidation reaction is preferably 30% or more, more preferably 35% or more, and much more preferably 40% or more, and is preferably less than 50% and more preferably 45% or less.

EXAMPLES (Production of Carboxylate)

Examples of polyoxyalkylene alkyl ether carboxylate were produced as Examples 1-5 and Comparative Examples 1-3. These examples are also shown in Tables 1-3. Conversions and dissolved oxygen concentrations were measured in the following manner:

Conversion: a sample was extracted from a suspension in a reaction system, and a catalyst was separated by filtration. A carboxyl group in the obtained filtrate was titrated with an EPTON method using a titration system (Metrohm 794 Basic Titrino, produced by METTLER TOLEDO) and a transmittance measurement device (Metrohm 622 Photometer, produced by METTLER TOLEDO), and a molarity of sodium polyoxyethylene alkyl ether carboxylate (hereinafter referred to as "sodium POE alkyl ether carboxylate") in the sample was obtained. A molarity of polyoxyethylene alkyl ether (hereinafter referred to as "POE alkyl ether") was obtained from the difference between a molarity of POE alkyl ether obtained from a loading weight of POE alkyl ether at a start of reaction and the above-mentioned molarity of sodium POE alkyl ether carboxylate. The obtained molarity was converted into a conversion in accordance with Equation (A).

A mass concentration was calculated by multiplying the molarity by a molecular weight.

Dissolved oxygen concentration: a corneal electrode-type dissolved oxygen meter (OM-51, produced by HORIBA, Ltd., 9520-10D Electrode, measurement range: 0-19.99 mg/L) was calibrated in the air, and then, an electrode tip was immersed in the sample so as to measure a dissolved oxygen concentration.

Example 1

First, 17.6 kg of POE alkyl ether in which 4 moles of ethylene oxide in average was added to lauryl alcohol, 48.8 kg of a sodium POE alkyl ether carboxylate aqueous solution (concentration of sodium POE alkyl ether carboxylate: 25.0% by mass) obtained as a reaction product of oxidation of the above POE alkyl ether with oxygen, 4.30 kg of 48% by mass of a sodium hydroxide aqueous solution, 3.50 kg of a powdery noble metal-supported catalyst (produced by Evonic Degussa Japan Co., Ltd., moisture content: 57.2% by mass) in which Pd (content: 4% by mass), Pt (content: 1% by mass), and Bi (content: 5% by mass) were supported on activated charcoal as a support, and 77.1 kg of deionized water were charged in a reaction vessel with a capacity of 300 L, and were stirred at 134 rpm with a stirring impeller (Maxblend impeller, produced by Sumitomo Heavy Industries, Ltd.) under an atmospheric pressure while being increased in temperature to 70° C., thereby preparing a suspension. This suspension had a total weight of 150 kg and a composition in which POE alkyl ether was 17.6 kg (11.7% by mass), sodium POE alkyl ether carboxylate was 12.1 kg (8.1% by mass), sodium hydroxide was 2.1 kg (1.4% by mass), the noble metal-supported catalyst was 1.5 kg (1.0% by mass), and water was 116.7 kg (77.8% by mass).

The depth of the suspension was 270 mm.

Next, with the stirring and the temperature control being continued, a nitrogen gas was supplied into the suspension at a supply rate of 500 mL/min for 16 minutes by bubbling, thereby reducing the amount of dissolved oxygen.

After the supply of the nitrogen gas had been stopped, an oxygen-containing gas (oxygen concentration: 90% by volume and nitrogen concentration: 10% by volume) was supplied into the suspension through an inlet with a diameter of 9.2 mm located at the bottom (at a depth of 270 mm) of the reaction vessel at a supply rate (a flow rate) of 5400 mL/min (where the supply rate of oxygen to the total mole number of POE alkyl ether and sodium POE alkyl ether carboxylate was 15 mol %/h), with the stirring and the temperature control being continued. The time when the supply of the oxygen-containing gas was started is defined as a reaction start. The conversion at the reaction start was 42%.

After a lapse of 1.0 hour from the reaction start, a sample was taken, the conversion was obtained, then the supply rate of the oxygen-containing gas (oxygen concentration: 90% by volume and nitrogen concentration: 10% by volume) was reduced to 2700 mL/min (where supply rate of oxygen to the total mole number of POE alkyl ether and sodium POE alkyl ether carboxylate was 7.5 mol %/h), and oxidation reaction was continued. The conversion was 56%.

The conversions after lapses of 2.0 hours and 3.0 hours from the reaction start were 70% and 83%, respectively.

After a lapse of 3.3 hours from the reaction start, the supply rate of an oxygen-containing gas (oxygen concentration: 90% by volume and nitrogen concentration: 10% by volume) was further reduced to 1800 mL/min (where the supply rate of oxygen to the total mole number of POE alkyl ether and sodium POE alkyl ether carboxylate was 5.0 mol %/h), and oxidation reaction was continued.

The conversions after lapses of 4.0 hours and 5.0 hours from the reaction start were 88% and 95%, respectively.

After a lapse of 6.0 hours from the reaction start, the supply of the oxygen-containing gas was stopped, and reaction is terminated. The conversion was 99%.

The suspension in the reaction vessel did not bubble from the reaction start to the reaction end.

Comparative Example 1

Oxidation reaction was started under the same conditions as Example 1. The conversion at the reaction start was 36%.

After a lapse of 1.7 hours from the reaction start, the suspension bubbled strongly in the reaction vessel to be blown out of the reaction vessel. Thus, the supply of the oxygen-containing gas was stopped to terminate the reaction. The conversion was 70%.

Example 2

First, 285.1 kg of POE alkyl ether, 950.5 kg of a sodium POE alkyl ether carboxylate aqueous solution (concentration of sodium POE alkyl ether carboxylate: 20.0% by mass) obtained as a reaction product of oxidation of the above POE alkyl ether with oxygen, 104.0 kg of 32% by mass of a sodium hydroxide aqueous solution, 53.90 kg of a powdery noble metal-supported catalyst (produced by Evonic Degussa Japan Co., Ltd., moisture content: 55.9% by mass) in which Pd (content: 4% by mass), Pt (content: 1% by mass), and Bi (content: 5% by mass) were supported on activated charcoal as a support, and 1011 kg of deionized water were charged in a reaction vessel with a capacity of 5000 L, and were stirred at 70 rpm with a stirring impeller (Super-Mix MR205, produced by Satake Chemical Equipment Mfg Ltd.) under an atmospheric pressure while being increased in temperature to 70° C., thereby preparing a suspension. This suspension had a total weight of 2400 kg and a composition in which POE alkyl ether was 285.1 kg (11.9% by mass), sodium POE alkyl ether carboxylate was 190.1 kg (7.92% by mass), sodium hydroxide was 33.28 kg (1.39% by mass), the noble metal-supported catalyst was 23.77 kg (0.990% by mass), and water was 1868 kg (77.8% by mass).

The depth of the suspension was 930 mm.

Next, with the stirring and the temperature control being continued, a nitrogen gas was blown into the suspension at a supply rate of 8.6 L/min for 15 minutes, thereby reducing the amount of dissolved oxygen.

After the supply of the nitrogen gas had been stopped, an oxygen-containing gas (oxygen concentration: 90% by volume and nitrogen concentration: 10% by volume) was supplied into the suspension through an inlet with a diameter of 16.1 mm located at the bottom (at a depth of 930 mm) of the reaction vessel at a supply rate (a flow rate) of 86.3 L/min (where the supply rate of oxygen to the total mole number of POE alkyl ether and sodium POE alkyl ether carboxylate was 15 mol %/h), with the stirring and the temperature control being continued. The time when the supply of the oxygen-containing gas was started is defined as a reaction start. The conversion at the reaction start was 42%.

The conversion after a lapse of 1.0 hour from the reaction start was 57%.

After a lapse of 1.6 hours from the reaction start, a sample was taken, the conversion was obtained, then the supply rate of the oxygen-containing gas (oxygen concentration: 90% by volume and nitrogen concentration: 10% by volume) was reduced to 43.2 L/min (where the supply rate of oxygen to the total mole number of POE alkyl ether and sodium POE alkyl ether carboxylate was 7.5 mol %/h), and oxidation reaction was continued. The conversion was 65%.

After a lapse of 2.0 hours from the reaction start, the conversion was 70%.

The supply rate of the oxygen-containing gas (oxygen concentration: 90% by volume and nitrogen concentration: 10% by volume) after a lapse of 2.6 hours from the reaction start was further reduced to 28.8 L/min (where the supply rate of oxygen to the total mole number of POE alkyl ether and sodium POE alkyl ether carboxylate was 5.0 mol %/h), and oxidation reaction was continued.

The conversions after lapses of 3.0 hours, 4.0 hours, and 5.0 hours from the reaction start, were 78%, 84%, and 89%, respectively.

After a lapse of 5.5 hours from the reaction start, the supply of the oxygen-containing gas was stopped to terminate the oxidation reaction.

The conversions after lapses of 6.0 hours, 7.0 hours, and 8.0 hours from the reaction start were 93%, 96%, and 98%, respectively.

The suspension in the reaction vessel did not bubble from the reaction start to the reaction end.

Comparative Example 2

Reaction was started under the same conditions as Example 2. The conversion at the reaction start was 40%.

After a lapse of 2.0 hours from the reaction start, a sample was taken, and the conversion was obtained. The conversion was 70%.

After a lapse of 2.8 hours from the reaction start, the supply rate of an oxygen-containing gas (oxygen concentration: 90% by volume and nitrogen concentration: 10% by volume) was reduced to 43.2 L/min (where the supply rate of oxygen to the total mole number of POE alkyl ether and sodium POE alkyl ether carboxylate was 7.5 mol %/h), and the oxidation reaction was continued.

After a lapse of 3.0 hours from the reaction start, the suspension bubbled strongly in the reaction vessel to be blown out of the reaction vessel. Thus, the supply of the oxygen-containing gas was stopped to terminate the reaction. The conversion was 83%. Although the sample for analysis was taken, the suspension in the vessel was blown out, and thus, a reaction product was not sufficiently collected.

Example 3

First, 2567 g of a POE alkyl ether aqueous solution in which POE alkyl ether obtained by adding 4 moles of ethylene oxide in average to lauryl alcohol and which had been diluted to have a concentration of 94% by mass with water, 8219 g of a sodium POE alkyl ether carboxylate aqueous solution (concentration of sodium POE alkyl ether carboxylate: 21.5% by mass) obtained as a reaction product of oxidation of the above POE alkyl ether with oxygen, 580.0 g of 48% by mass of a sodium hydroxide aqueous solution, 432 g of a powdery noble metal-supported catalyst (produced by Evonic Degussa Japan Co., Ltd., moisture content: 57.2% by mass) in which Pd (content: 4% by mass), Pt (content: 1% by mass), and Bi (content: 5% by mass) were supported on activated charcoal as a support, and 8351 g of deionized water were charged in a reaction vessel with a capacity of 30 L, and were stirred at 50 rpm with a stirring impeller (Super-Mix MR205, produced by Satake Chemical Equipment Mfg Ltd.) under an atmospheric pressure while being increased in temperature to 70° C., thereby preparing a suspension. This suspension had a total weight of 20149 g. The suspension had a composition in which POE alkyl ether was 2413 g (12.0% by mass), sodium POE alkyl ether carboxylate was 1767 g (8.8% by mass), sodium hydroxide was 278.0 g (1.4% by mass), the noble metal-supported catalyst was 185 g (0.9% by mass), and water was 15506 g (77.0% by mass).

The depth of the suspension was 226 mm.

Next, with the stirring and the temperature control being continued, a nitrogen gas was supplied into the suspension at a supply rate of 67.9 mL/min by bubbling for 15 minutes.

After the supply of the nitrogen gas had been stopped, an oxygen-containing gas (oxygen concentration: 90% by volume and nitrogen concentration: 10% by volume) was supplied into the suspension through an inlet with a diameter of 9.2 mm located at the bottom (at a depth of 226 mm) of the reaction vessel at a supply rate (a flow rate) of 722 mL/min (where the supply rate of oxygen to the total mole number of POE alkyl ether and sodium POE alkyl ether carboxylate was 15 mol %/h), with the stirring and the temperature control being continued. The time when the supply of the oxygen-containing gas was started is defined as a reaction start. The conversion at the reaction start was 36.5%.

After a lapse of 2.0 hours from the reaction start, a sample was taken, the conversion was obtained, then the supply rate of the oxygen-containing gas (oxygen concentration: 90% by volume and nitrogen concentration: 10% by volume) was reduced to 481 mL/min (where the supply rate of oxygen to the total mole number of POE alkyl ether and sodium POE alkyl ether carboxylate was 10 mol %/h), and oxidation reaction was continued. The conversion was 58%.

After a lapse of 5.7 hours from the reaction start, the supply of the oxygen-containing gas was stopped to terminate the reaction. The conversion was 84%.

Although the suspension slightly bubbled at the end of reaction, this bubbling had no significant influence on collection of the reaction product.

Example 4

Reaction was started under the same conditions as Example 3.

After a lapse of 2.0 hours from the reaction start, a sample was taken, the conversion was obtained, then the supply rate of an oxygen-containing gas (oxygen concentration: 90% by volume and nitrogen concentration: 10% by volume) was reduced to 241 mL/min (where the supply rate of oxygen to the total mole number of POE alkyl ether and sodium POE alkyl ether carboxylate was 5 mol %/h), and oxidation reaction was continued. The conversion was 56%.

After a lapse of 10 hours from the reaction start, the supply of the oxygen-containing gas was stopped to terminate the reaction. The conversion was 91%.

Example 5

Reaction was started under the same conditions as Example 3 except that the amount of a supplied oxygen-containing gas at a reaction start was 548 mL/min (where the supply rate of oxygen to the total mole number of POE alkyl ether and sodium POE alkyl ether carboxylate was 11 mol %/h).

After a lapse of 2.0 hours from the reaction start, a sample was taken, the conversion was obtained, then the supply rate of the oxygen-containing gas (oxygen concentration: 90% by volume and nitrogen concentration: 10% by volume) was reduced to 361 mL/min (where the supply rate of oxygen to the total mole number of POE alkyl ether and sodium POE alkyl ether carboxylate was 7.5 mol %/h), and oxidation reaction was continued. The conversion was 60%.

After a lapse of 9 hours from the reaction start, the supply of the oxygen-containing gas was stopped to terminate the reaction. The conversion was 97%.

The suspension in the reaction vessel did not bubble from the reaction start to the reaction end.

Comparative Example 3

Reaction was started under the same conditions as Example 3 except that the amount of a supplied oxygen-containing gas at a reaction start was 241 mL/min (where the supply rate of oxygen to the total mole number of POE alkyl ether and sodium POE alkyl ether carboxylate was 5 mol %/h).

After a lapse of 4.1 hours from the reaction start, the amount of the reaction liquid increased so that this liquid could not be stirred any more. In addition, the suspension bubbled strongly in the reaction vessel to be blown out of the reaction vessel. Thus, the supply of the oxygen-containing gas was stopped to terminate the reaction. The conversion was 55%.

TABLE 1

| | Example 1 | | Comparative Example 1 | | Example 2 | | Comparative Example 2 | |
|---|---|---|---|---|---|---|---|---|
| | Depth mm | | | | | | | |
| | 270 | | 270 | | 930 | | 930 | |
| Time h | Oxygen Supply Rate mol %/h | Conversion % | Oxygen Supply Rate mol %/h | Conversion % | Oxygen Supply Rate mol %/h | Conversion % | Oxygen Supply Rate mol %/h | Conversion % |
| 0.0 | 15 | 42 | 15 | 36 | 15 | 42 | 15 | 40 |
| 1.0 | 15→7.5 | 56 | | | 15 | 57 | | |
| 1.6 | | | | | 15→7.5 | 65 | | |
| 1.7 | | | 15→0 | 70 | | | | |
| 2.0 | 7.5 | 70 | | | 7.5 | 70 | 15 | 70 |
| 2.6 | | | | | 7.5→5.0 | | | |
| 2.8 | | | | | | | 15→7.5 | |
| 3.0 | 7.5 | 83 | | | 5.0 | 78 | 7.5→0 | 83 |
| 3.3 | 7.5→5.0 | | | | | | | |
| 4.0 | 5.0 | 88 | | | 5.0 | 84 | | |
| 5.0 | 5.0 | 95 | | | 5.0 | 89 | | |
| 5.5 | | | | | 5.0→0 | | | |
| 6.0 | 5.0→0 | 99 | | | 0 | 93 | | |
| 7.0 | | | | | 0 | 96 | | |
| 8.0 | | | | | 0 | 98 | | |

Oxygen Supply Rate: Supply rate [mol %/h] of oxygen to charged mole number of POE alkyl ether Conversion (%) = Total molarity (mol/L) of POE alkyl ether carboxylic acid and the salt 5 thereof/(molarity (mol/L) of POE alkyl ether + total molarity (mol/L) of POE alkyl ether carboxylic acid and the salt thereof)

TABLE 2

| | Example 3 | | Example 4 | | Example 5 | | Comparative Example 3 | |
|---|---|---|---|---|---|---|---|---|
| | Depth mm | | | | | | | |
| | 226 | | 226 | | 226 | | 226 | |
| Time h | Oxygen Supply Rate mol %/h | Conversion % | Oxygen Supply Rate mol %/h | Conversion % | Oxygen Supply Rate mol %/h | Conversion % | Oxygen Supply Rate mol %/h | Conversion % |
| 0.0 | 15 | 36.5 | 15 | 36.5 | 11 | 36.5 | 5 | 36.5 |
| 2.0 | 15→10 | 58 | 15→5 | 56 | 11→7.5 | 60 | | |
| 4.1 | | | | | | | 5→0 | 55 |
| 5.7 | 10→0 | 84 | | | | | | |
| 10.0 | | | 5→0 | 91 | 7.5→0 | 97 | | |

Oxygen Supply Rate: Supply rate [mol %/h] of oxygen to charged mole number of POE alkyl ether Conversion (%) = Total molarity (mol/L) of POE alkyl ether carboxylic acid and the salt thereof/(molarity (mol/L) of POE alkyl ether + total molarity (mol/L) of POE alkyl ether carboxylic acid and the salt thereof)

TABLE 3

| | Example 1 | Comparative Example 1 | Example 2 | Comparative Example 2 | Example 3 | Example 4 | Example 5 | Comparative Example 3 |
|---|---|---|---|---|---|---|---|---|
| Reaction Vessel Capacity (L) | 300 | 300 | 5000 | 5000 | 30 | 30 | 30 | 30 |
| Depth (mm) | 270 | 270 | 930 | 930 | 226 | 226 | 226 | 226 |
| Initial Oxygen Flow Rate (mol %/h) | 15 | 15 | 15 | 15 | 15 | 15 | 11 | 5 |
| Conversion (%) at Oxygen Flow Rate Switch | 56 | — | 65 | — | 58 | 56 | 60 | — |
| Oxygen Flow Rate (mol %/h) After Switch | 7.5 | — | 7.5 | 7.5 | 10 | 5 | 7.5 | — |
| Switch Time (h) | 1.0 | — | 1.6 | 2.8 | 2.0 | 2.0 | 2.0 | — |
| Final Conversion (%) | 99 | 70 | 98 | 83 | 84 | 91 | 97 | 55 |
| Reaction End Time (h) | 6.0 | 1.7 | 8.0 | 3.0 | 5.7 | 10 | 10 | 4.1 |
| Slurry State at the End of Reaction | No Problem | Vigorous Bubbling | No Problem | Vigorous Bubbling | No Problem | No Problem | No Problem | Vigorous Bubbling |

Conversion (%) = Total molarity (mol/L) of POE alkyl ether carboxylic acid and the salt thereof/(molarity (mol/L) of POE alkyl ether + molarity (mol/L) of POE alkyl ether carboxylic acid and the salt thereof)

The foregoing results show that in each Example, the suspension did not bubble and production could continue, and thus, target sodium POE alkyl ether carboxylate could be produced with high yield.

Industrial Applicability

The present invention is useful for a method for producing polyoxyalkylene alkyl ether carboxylic acid and a salt thereof.

The invention claimed is:

1. A method for producing polyoxyalkylene alkyl ether carboxylic acid or a salt thereof, the method comprising an oxidation reaction process of oxidizing polyoxyalkylene alkyl ether with oxygen by supplying an oxygen-containing gas to a suspension that has a depth of 200 mm or more and includes 10 to 40% by mass of polyoxyalkylene alkyl ether, the suspension including 0.9 to 20% by mass of a powdery noble metal-supported catalyst comprising a noble metal supported on a support,
wherein in the oxidation reaction process, in a period in which a conversion expressed by Equation (A) is greater than or equal to 50% and less than 70%, a supply rate of the oxygen-containing gas is reduced such that a supply rate of oxygen to a total mole number of polyoxyalkylene alkyl ether, polyoxyalkylene alkyl ether carboxylic acid, and the salt thereof is reduced from a range greater than 10 mol %/h and less than or equal to 15 mol %/h to a range greater than or equal to 1 mol %/h and less than or equal to 10 mol %/h,

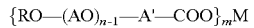

conversion(%)=c2×100/(c1+c2)  (A)

wherein c1 is a molarity (mol/L) of polyoxyalkylene alkyl ether, and C2 is a total molarity (mol/L) of polyoxyalkylene alkyl ether carboxylic acid and the salt thereof.

2. The method of claim 1, wherein a total amount of polyoxyalkylene alkyl ether, polyoxyalkylene alkyl ether carboxylic acid, and the salt thereof is 15-70% by mass of a total amount of the suspension.

3. The method of claim 1, wherein in the oxidation reaction process, an oxygen concentration in the oxygen-containing gas to be supplied to the suspension is 50-100% by volume.

4. The method of claim 1, wherein in the oxidation reaction process, the conversion expressed by Equation (A) at an end of reaction is 80% or more.

5. The method of claim 1, wherein the noble metal is at least one selected from elements of a platinum group.

6. The method of claim 1, wherein in the oxidation reaction process, a reaction temperature during supply of the oxygen-containing gas to the suspension is 20-100° C.

7. The method of claim 1, wherein polyoxyalkylene alkyl ether carboxylate is expressed by:

{RO—(AO)$_{n-1}$—A'—COO}$_m$M

[where R is a hydrocarbon group having 4-30 carbon atoms, AO is an alkyleneoxy group having 2-4 carbon atoms, n is an average addition mole number of AO and ranges from 1 to 100, A' is an alkylene group having 1-3 carbon atoms, M is a cation or a hydrogen ion, and m is a valence of M].

8. The method of claim 1, wherein in the oxidation reaction process, a ratio (d/D) of a depth (d) from a liquid level at which the oxygen-containing gas is supplied to the suspension in a static state at an end of filling with a reaction material to the depth (D) to the suspension is 0.1-1.

9. The method of claim 1, wherein in the oxidation reaction process, the supply rate of the oxygen-containing gas to the suspension is reduced in a plurality of steps at a plurality of stages.

10. The method of claim 1, wherein in the oxidation reaction process, the conversion expressed by Equation (A) at a start of an oxidation reaction is greater than or equal to 30%.

11. The method of claim 1, wherein in the oxidation reaction process, a reaction pressure as a gauge pressure is 0-1.0 MPa.

12. The method of claim 1, wherein in the oxidation reaction process, the supply rate of the oxygen-containing gas after reduction of the supply rate of the oxygen-containing gas is such that the supply rate of oxygen to the total mole number of polyoxyalkylene alkyl ether, polyoxyalkylene alkyl ether carboxylic acid, and the salt thereof is 2-8 mol %/h.

13. The method of claim 1, wherein in the oxidation reaction process, the supply rate of the oxygen-containing gas after reduction of the supply rate of the oxygen-containing gas is such that the supply rate of oxygen to the total mole number of polyoxyalkylene alkyl ether, polyoxyalkylene alkyl ether carboxylic acid, and the salt thereof is 5-8 mol %/h.

14. The method of claim 1, wherein in the oxidation reaction process, an initial supply rate of the oxygen-containing gas is such that the supply rate of oxygen to the total mole number of polyoxyalkylene alkyl ether, polyoxyalkylene alkyl ether carboxylic acid, and the salt thereof is greater than 11 mol %/h and less than or equal to 15mol %/h.

15. The method of claim 1, wherein a concentration of polyoxyalkylene alkyl ether in the suspension is greater than or equal to 1% by mass and less than or equal to 40% by mass.

16. The method of claim 1, wherein a concentration of polyoxyalkylene alkyl ether in the suspension is greater than or equal to 5% by mass and less than or equal to 35% by mass.

17. The method of claim 1, wherein a concentration of polyoxyalkylene alkyl ether in the suspension is greater than or equal to 10% by mass and less than or equal to 30% by mass.

* * * * *